US00PP10635P

United States Patent [19]

Schumann et al.

[11] Patent Number: Plant 10,635

[45] Date of Patent: Oct. 6, 1998

[54] GERANIUM PLANT NAMED 'FLOFETTI'

[75] Inventors: Ingeborg Schumann, Albstadt; Angelika Utecht, Montabaur, both of Germany

[73] Assignee: Florfis AG, Binningen, Switzerland

[21] Appl. No.: 819,372

[22] Filed: Mar. 17, 1997

[51] Int. Cl.[6] ..... A01H 5/00

[52] U.S. Cl. ..... Plt./87.12

[58] Field of Search ..... Plt./87.12

[56] References Cited

PUBLICATIONS

GTITM UPOV–ROM (Apr. 1997), citation 'Flofetti', German Plant Breeder's Rights Certificate PEL 00996, filed Dec. 1994, 1997.

*Primary Examiner*—Howard J. Locker
*Assistant Examiner*—Melissa L. Kimball
*Attorney, Agent, or Firm*—Foley & Lardner

[57] ABSTRACT

A new and distinct cultivar of geranium plant named 'Flofetti', particularly characterized by the combined features of large, intense pink flowers in compact inflorescences, relatively small, glossy, bright green foliage with distinct zonation, and medium tall, compact and bush plant habit.

1 Drawing Sheet

The present invention comprises a new and distinct cultivar of geranium, botanically known as *Palargonium peltatum,* and hereinafter referred to by the cultivar name 'Flofetti'.

'Flofetti' is a product of a planned breeding program which had the objective of creating new geranium cultivars with pink flower color and medium growth characteristics.

'Flofetti' was originated from a hybridization made by the inventor Ingeborg Schumann in a controlled breeding program in Galdar, Gran Canaria, Spain in 1987. The female parent was and unnamed hybrid derived from crossings between the violet pink colored cultivar 'Italian Gem', the rose flowered cultivar 'El Gaucho', and the cultivar 'Princetown', which has dark pink semi-double flowers. The male parent of 'Flofetti' was the commercial cultivar 'Solidor', characterized by light pink semi-double flowers, medium green foliage with only very weak zonation, and very compact and bushy plant habit.

'Flofetti' was discovered and selected as one flowering plant within the progeny of the stated cross by Ingeborg Schumann in 1988 in a controlled environment in Galdar, Gran Canaria, Spain. The first act of asexual reproduction of 'Flofetti' was accomplished when vegetative cuttings were taken from the initial selection in June 1990 in a controlled environment in Galdar, Gran Canaria, Spain, by, or under the supervision of, inventor Angelika Utecht.

Horticultural examination of plants grown from this clone initiated in May 1991 in Hillscheid, Federal Republic of Germany and continuing thereafter, has demonstrated that the combination of Characteristics as herein disclosed for 'Flofetti' are firmly fixed and are retained through successive generations of asexual reproduction.

'Flofetti' has not been observed under all possible environmental conditions. The phenoytpe may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice. The following traits have been repeatedly observed and are determined to be basic characteristics of 'Flofetti', which in combination distinguish this geranium as a new and distinct cultivar:

1. Deep pink flowers with distinct purple markings.
2. Large double flowers, but open flower shape.
3. Small, bright green, glossy leaves with distinct zonation.
4. Medium vigor, compact and bushy plant habit.
5. Medium to early flower response.

Of the many commercial cultivars known to the present inventors, the most similar in comparison to 'Flofetti' are the unpatented cultivar 'Rigi' and the patented cultivar 'Fisgeti', disclosed in U.S. Plant Pat. No. 9,412. In general comparison to 'Rigi', 'Flofetti' has smaller and differently shaped leaves with stronger lobes and more ring-shaped zonation. 'Flofetti' also has somewhat smaller flowers and grows more compact with better branching ability and with shorter internodes.

In comparison to 'Fisgeti', flowers of 'Flofetti' are slightly more bluish in color, and the foliage is different. The leaves of 'Flofetti' are smaller with more rounded tips, stronger zonation, and entire margins. In contrast, the leaves of 'Fisgeti' are maple-shaped, and have notches near the tips.

The accompanying photographic drawing shows typical flower and foliage characteristics of 'Flofetti', with colors being as true as possible to illustrations of this type.

In the following description color references are made to The Royal Horticultural Society Color Chart (RHS). The color values were determined indoors from flowers taken from plants grown in a greenhouse in May 1995 in Hillscheid, Germany.

Classification:

*Botanical.*—A hybrid of the species *Pelargonium peltatum* l'hert.

*Commerical.*—Ivy geranium, cv. 'Flofetti'.

Inflorescence

Umbel:

*Shape.*—Semi-spherical.

*Average diameter.13* 106 mm.

*Peduncle length.*—168 mm.

*Pedicel length.*—33 mm.

*Pedicel color.*—Partly dark red.

*Number of flowers per umbel.*—11.

Corolla:

*Average diameter.*—52 mm.

*Number of petals.*—11–15.
*Number of petaloids.*—2–3.
*Color* (*general tonality from a distance of three meters*) .—Bluish pink.
*Color of upper petals.*—67 B, color may fade as flowers mature.
*Markings on upper petals.*—Two purple veins with lighter stripe between.
*Color of lower petals.*—67 B.
*Color of lower surface of petals.*—67 D.
*Color of sepals.*—Light green, largest sepal infused with anthocyanin.
*Number of sepals.*—5–6.

Bud:
*Shape.*—Elliptic.
*Color* (*adaxial*).—Green.
*Color* (*Abaxial*).—Salmon pink, marbled.

Reproductive organs:
*Androecium.*—About 5 fertile anthers, white filaments, orange pollen.
*Gynoecium.*—5–6 lobed stigma, pink style and stigma.
*Seed set.*—No spontaneous seed set was observed.

Spring flowering response period: In Hillscheid, Germany in 1995, plants had on average 0.5 flowers opened 15 weeks after planting of unrooted cuttings (pinched plants).

Outdoor flower production: The flower count in 1994 in Hillscheid, Germany indicated about 100 umbels per plant for May through August observation period.

Durability: Good shatter resistance; rain resistance relatively good for a double flowered variety.

Plant

Foliage:
*Form.*—Ivy shaped with rounded tips.
*Margin.*—Entire.
*Upper surface.*—Smooth, glossy.
*Size of leaf.*—70 mm.
*Color of upper surface.*—Medium green, approximately 137 C.
*Color of zonation.*—Brown, about 166 A.
*Tolerance of botrytis.*—Average.

General Appearance and form:
*Internode length.*—50 mm.
*Branching pattern.*—7.4 branches per plant, based on 16 week old plants.
*Length of plants.*—75 cm, in September based on 35 week old plants.

I claim:

1. A new and distinct cultivar of geranium plant named 'Flofetti', as illustrated and described.

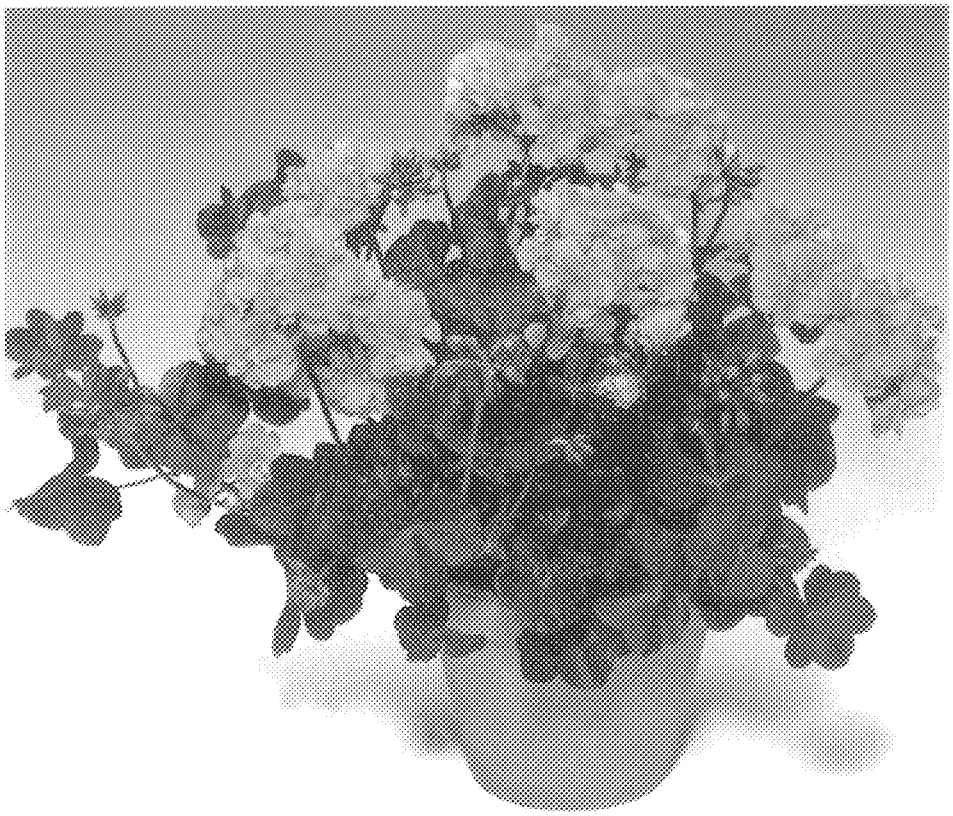

* * * * *